United States Patent [19]

Stewart et al.

[11] Patent Number: 4,737,363

[45] Date of Patent: Apr. 12, 1988

[54] BACTEROIDES NODOSUS VACCINE

[75] Inventors: David J. Stewart, Hawthorn East; Alexander A. Kortt, Strathmore, both of Australia

[73] Assignee: Commonwealth Scientific and Industrial Research Organization, Australia

[21] Appl. No.: 810,152

[22] Filed: Dec. 18, 1985

[30] Foreign Application Priority Data

Dec. 24, 1984 [AU] Australia ............................ PG8700

[51] Int. Cl.[4] .................... A61K 37/547; A61K 39/02
[52] U.S. Cl. ............................ 424/94.63; 424/94.64; 424/94.1; 424/94.2; 424/88; 424/92; 435/23; 435/219
[58] Field of Search ............... 424/94, 88, 92, 94.1, 424/94.2, 94.63, 94.64; 435/23, 219

[56] References Cited

PUBLICATIONS

Kortt et al, *Res. in Vet. Sci.*, 1983, pp. 171–174, vol. 35.
Kortt et al, *Aust. J. Biol. Science*, 1982, 35, pp. 481–489.
Depiazzi, *Vet. Microbiol.*, 9, 1984, pp. 227–236.
Every, *J. Gen. Microbiol.*, 128, 1982, pp. 809–812.
Every et al, *N. Zealand Vet. J.*, vol. 30, 1982, pp. 156–158.
Stewart, *Commonwealth of Australia*, vol. 24, 1978, 14–19.
N. Z. Journal of Agricultural Research, (1976), 19: 317–322, Broad, T. E. and Skerman, T. M.
Australian Veterinary Journal, (1983), 60: 331–334, Claxton, P. D., Ribeiro, L. A. and Egerton, J. R., Annals of the New York Academy of Sciences, (1964), 121: 404–427, Davis, B. J.
Australian Veterinary Journal, (1979), 55: 25–28, Depiazzi, L. J. and Richards, R. B.
Australian Veterinary Journal, 1983, 60: 111–116, Fahey, K. J., McWaters, P. G., Stewart, D. J., Peterson, J. E. and Clark, B. L.
Analytical Biochemistry, (1972), 48: 422–427, Hartree, E. F.
Australian Journal of Biological Sciences, (1983), 36: 15–20, O'Donnell, I. J., Stewart, D. J. and Clark, B. L.
Research in Veterinary Science, (1978), 24: 14–19, Stewart, D. J.
Australian Veterinary Journal, (1983a), 60: 83–85, Stewart, D. J., Clark, B. L., Emery, D. L., Peterson, J. E. and Fahey, K. J.
Australian Advances in Veterinary Science, (1982), pp. 219–222, Stewart, D. J., Clark, B. L. and Jarrett, R. G.
Australian Veterinary Journal, (1985), (Accepted for publication), Stewart, D. J., Clark, B. L., Peterson, J. E., Emery, D. L., Smith, E. F., et al.
Research in Veterinary Science, (1982), 32: 140–147, Stewart, D. J., Clark, B. L., Peterson, J. E., Griffiths, D. A. and Smith, E. F.
Research in Veterinary Science, (1983b), 35: 130–137, Stewart, D. J., Clark, B. L., Peterson, J. E., Griffiths, D. A., Smith, E. F. & O'Donnell, I. J.
Research in Veterinary Science, (1981), 30: 32–37, Thorley, C. M. and Egerton, J. R.

Primary Examiner—John Kight
Assistant Examiner—Garnette D. Draper
Attorney, Agent, or Firm—Sughrue, Mion, Zinn, Macpeak and Seas

[57] ABSTRACT

A vaccine for use in the prevention or treatment of foot-rot comprises an immunologically effective amount of at least one protease, particularly an extracellular serine protease, of *Bacteroides nodosus* as an active component thereof, and optionally an acceptable pharmaceutical or veterinary carrier therefor.

27 Claims, No Drawings

BACTEROIDES NODOSUS VACCINE

This invention relates to a prophylactic and therapeutic treatment of ovine foot-rot and in particular relates to a vaccine effective in such treatment of ovine foot-rot.

Ovine foot-rot is a contagious disease of the sheep's foot which is characterised by separation of the hoof from the living epidermal tissues due to a spreading infection in the interdigital skin and beneath the horn. The essential causitive agent of ovine foot-rot infection is the anaerobic Gram-negative bacterium *Bacteroides nodosus*. The disease is of considerable economic significance throughout the temperate areas of the world where sheep are raised. In Australia alone the estimated losses due to foot-rot amount to millions of dollars annually.

Classification of strains of *B.nodosus* in serogroups and subgroups is based on agglutinogens which are present on surface filaments termed pili or fimbriae. The pili induce a high level of protection in vaccinated sheep against homologous serogroups of *B.nodosus* (Stewart 1978, Every and Skerman 1982; Stewart et al 1982, 1983a, b). Since there are at least 8 serogroups, the current commercial vaccines contain killed whole cells of 8-10 well piliated strains representative of all the known serogroups (Claxton et al, 1983). These vaccines are more expensive than other vaccines used in sheep partly due to the need for the incorporation of a multiple number of strains in the vaccine and partly due to the fastidious growth requirements and relatively sparse growth of *B.nodosus* in liquid media. Pilus expression tends to be variable and, especially with some strains, the irreversible loss of pili from cells following subculture in liquid medium is a major problem to manufacturers. There is also a physical limit to the number of strains which can be incorporated in commercial foot-rot vaccines and the efficacy of the whole vaccine could decrease if additional strains need to be incorporated. Multivalent whole bacterial cell vaccines are also not satisfactory because of the large size of the granulomas formed at the site of inoculation.

Although homologous protection is superior to that obtained against heterologous strains, nevertheless some cross-protection against heterologous serogroups has been obtained with whole cell vaccines (Thorley and Egerton 1981; Stewart et al 1983a; Stewart et al 1985). The identification of the nature and location of the cross-protective antigens may facilitate the rational selection of a reduced number of vaccine serotypes based on the presence of serogroup-specific pilus antigens and cross-protective non-pilus antigens, the latter being common to (shared by) at least some serogroups. Alternatively vaccination of sheep with large amounts of cross-protective antigens may enable a high level of protection to be induced against a wide range of serogroups.

It has now been discovered that the proteases, particularly the extracellular serine proteases produced by *B.nodosus* may be used to induce cross-protection against both heterologous serogroups and the serogroup from which the proteases are derived.

Thus, in accordance with one aspect of the present invention there is provided a vaccine for use in the prevention or treatment of foot-rot comprising an immunologically effective amount of at least one protease, particularly an extracellular serine protease, of *Bacteroides nodosus* as an active component thereof, and optionally an acceptable pharmaceutical or veterinary carrier therefor.

In another aspect, this invention provides a method of preventing or treating foot-rot, which comprises the administration of a vaccine as described above.

The carrier may be any suitable pharmaceutical or veterinary carrier, the exact form of which will depend on the administration technique to be used to obtain effective vaccination. The means of administration may be oral, subcutaneous, intravenous, intramuscular, intraperitoneal, by aerosol, suppository, bolus or by any other suitable procedure. The vaccine may include a known adjuvant, such as an oil, saponin-aluminium hydroxide, or aluminium hydroxide-oil adjuvant, to improve its efficacy. The adjuvant may itself be the carrier, and the adjuvant/carrier/means of administration will be chosen to enhance the antibody response. One advantage of the use of the present vaccine is that the size of the granulomatous reaction at the site of a subcutaneous inoculation can be substantially reduced when the oil-adjuvant vaccine contains purified antigens rather than whole organisms.

In yet another aspect of the present invention, there is provided a method of detecting antibodies in sheep serum, which comprises the use of at least one protease of *B.nodosus* as an antigen in an immunoassay. Full details of the methods by which such immunoassays can be carried out are well known in the art, and are accordingly not described in detail here. These methods include, for example, the well known ELISA and radioimmunoassays.

*Bacteroides nodosus* has been shown to elaborate extracellular proteases (Broad and Sherman 1976; Kortt et al 1982; 1983; Depiazzi and Rood 1984). These are serine proteases being completely inhibited by phenyl methylsulfonyl fluoride (PMSF), while N-tosyl-L-phenylalanyl chloromethylketone (TPCK), a specific inhibitor of o-chymotrypsin ($10^{-4}$M), inhibits approximately 30% of the activity of *B.nodosus* proteases. Reducing agents do not significantly affect their activity. The protease activity is inhibited by the metal ion chelator EDTA but not by 1,10-phenanthroline indicating that divalent ions such as $Ca^{2+}$ are essential for activity but not heavy metal ions such as $Zn^{2+}$ and $Fe^{2+}$. Proteolytic activity is rapidly lost below about pH6.0 and the proteases are stable to heating to 50° C. but above 60° C. their activity rapidly decreases. However, virulent proteases and proteases from a proportion of intermediate strains in trypticase-arginine-serine (TAS) broth cultures have greater stability than benign proteases in TAS broth (Depiazzi and Richards 1979; Kortt et al 198; Stewart et al 1982). Calcium ions increase the thermostability of the proteases (Stewart et al 1982; Depiazzi and Rood 1984), and this is most marked with benign strains.

The proteases digest casein, hide powder azure and $^{125}$I-labelled elastin as well as denatured haemoglobin. They do not hydrolyse the synthetic substrate α-N-benzoyl-L-arginine ethyl ester or N-benzoyl-L-tyrosine ethyl ester. The specific activity per microgram of purified proteases of *B.nodosus* with casein as substrate is about the same as that obtained with bovine trypsin.

The proteases may be purified from a concentrated culture supernatant from trypticase-arginine-serine (TAS) broth cultures containing 0.15% $CaCl_2$ which were grown anaerobically at 37° C. for 2 to 4 days. The cultures are centrifuged to remove cells and insoluble material and concentrated 100–500 fold either on Diaflo hollow fibre H10P3-20 and HIP3-20 cartridges (Amicon) (mol. wt. cut-off about 3000) or Diaflo spiral-wound ultrafiltration membrane cartridges models S10Y10 or S1Y10 (Amicon) (mol.wt. cut-off about 10,000) and/or in an Amicon ultrafiltration cell using a Diaflo YM-10 membrane (mol.wt. cut-off about 10,000). The concentrate is chromatographed on a column of Sephadex G100 at 4° C. equilibrated with 0.02M Tris HCl–5 mM $CaCl_2$, pH 8.0 buffer. The bulk of the proteolytic activity elutes as a single broad peak at a Ve/Vc ratio of approx.0.6, where Ve=elution volume of the proteolytic activity and Vc=column volume, and the active fractions are pooled, concentrated and dialysed against 0.01M Tris HCl–5 mM $CaCl_2$, pH 8.5 buffer at 4° C. This material is then fractionated on a column of DEAE-Sephadex A-25 or DEAE-Sephacel equilibrated with 0.01M Tris HCl–5 mM $CaCl_2$, pH 8.5 buffer with a 0 to 0.1M NaCl gradient at 4° C. The peaks with protease activity as assessed with hide powder azure substrate are concentrated and their purity assessed by non-dissociating polyacrylamide gels at pH 8.8 using the buffer system of Davis (1964).

On sodium dodecyl sulphate polyacrylamide gel electrophoresis (SDS-PAGE) the proteases have an apparent molecular weight of approximately 37,000 to 43,000. The proteases are a mixture of isoenzymes which can be separated into 4 to 5 unique bands (Kortt et al 1983) on the basis of differences in ionic charges present on 5 to 7.5% polyacrylamide gels using the non-dissociating buffer system of Davis (1964). The protease bands are detected by placing the polyacrylamide gel slab on a layer of gelatin-agar and allowing hydrolysis of the gelatin to occur. After 2 hours at 37° C., the unhydrolysed gelatin is precipitated with mercuric chloride in acid (Kortt et al 1983). Alternatively unstained gel slices are assayed for proteolytic activity with hide powder azure and the location of activity compared with a duplicate gel stained for protein with Coomassie brilliant blue G250.

Benign and virulent isolates of *B.nodosus* can be distinguished from each other by differences in their protease isoenzyme patterns after polyacrylamide gel electrophoresis (Every 1982; Kortt et al 1983). Virulent isolates of *B.nodosus* possess 4 isoenzyme bands whereas benign strains have a zymogram pattern with 5 bands of activity of which the first 4 bands have lower mobility than protease bands 1, 2 and 3 of virulent strains. Bands 5 from benign and virulent strains have similar electrophoretic mobilities. Virulent strains can be divided into types 1 and 2 on the basis of variation in the virulent zymogram pattern. All virulent strains contain bands 1, 2 or 3. Compared with type 1, the type 2 strains lack band 5 but have an additional band (4) migrating between bands 3 and 5.

In zymograms, the protease isoenzyme bands of virulent and a proportion of intermediate strains have the same stability patterns when TAS broth cultures are sampled after 2, 4, 8, 12, 16 and 20 days of anaerobic incubation at 37° C. In these cultures, band 1 and 5 activities decrease markedly after day 8, but bands 2 and 3 persist to day 20 with some loss of resolution after day 16. The proteases of benign cultures are less stable at 37° C. Benign band 2 activity decreases from day 4 and little activity remains at day 8. Although band 3 activity persists to day 20, it markedly decreases after day 12. Benign band 5 activity decreases after day 8 and disappears by day 16, as with virulent band 5. $CaCl_2$ does not influence the type of zymogram pattern obtained with virulent, intermediate or benign strains, but prevents the disappearance of band 5 during prolonged incubation. $CaCl_2$ does not prevent the disappearance of band 1 in the virulent and intermediate strains, nor of bands 2 and 3 in the benign strains.

The proteases from virulent strain 198 have been purified to homogeneity and used in vaccine experiments as a mixture of purified proteases (e.g. isoenzyme bands V2, 3 and 5) and as single protease (e.g. isoenzyme band V2). It will be appreciated, that the present invention extends to the use of both individual purified protease isoenzyme bands and mixed protease isoenzyme bands including, for example, isoenzyme bands 1, 2, 3, 4 and/or 5 from other virulent and/or intermediate and/or benign strains.

The following examples illustrate the use of *B.nodosus* proteases in the preparation of vaccines, and in the use of such vaccines in inducing protection in sheep.

EXAMPLE 1

The experiment was conducted on irrigated pasture at the CSIRO Werribee Field Station utilising flood irrigation to provide sufficient moisture for both pasture growth and transmission of foot-rot.

The Merino sheep were vaccinated twice subcutaneously in the neck region with an interval of 4 weeks between the injections.

Vaccines

The strain 198 and 216 cells used for preparing the various fractions have been grown in modified Eugon broth.

1. Strain 198 whole cells $2.15\times10^9$ cells per dose.
2. Strain 216 whole cells $2.15\times10^9$ cells per dose.
3. Strain 198 purified pili 25μ per dose.
4. Strain 198 purified protease 50μ per dose.
5. Strain 198 depiliated cell walls 350μ per dose.
6. Strain 198 outer membrane complex (OMC) with high pilus content 108μ per dose.

All fractions were diluted in PBS to the required concentration. The amount of protein in each of the fractions was estimated by a modified Lowry method (Hartree 1972) whereas the amount of pili was estimated by ELISA (Fahey et al 1983).

The aqueous phase of the vaccines was emulsified with incomplete Freund's adjuvant (Difco) in the ratio 1:2.

There were 18 sheep per vaccine group and 18 sheep in the control group. The sheep were randomly allocated to each of the groups on a bodyweight basis. All groups were run as one flock and were exposed at the time of the second vaccination to donor sheep previously infected with *B.nodosus* strain 216 which belongs to a serogroup (E) distinct from that of strain 198 (serogroup A) i.e. they possess antigenically unrelated pilus agglutinogens.

The feet of all sheep were inspected and the lesions evaluated by the scoring system of Stewart et al (1982).

Results

Inspection of feet 56 days after both challenge and vaccination showed the following results.

| | % with foot-rot (lesions ≧2) | |
|---|---|---|
| Vaccine Group | feet | sheep |
| 1. Strain 198 whole cells | 5.6 | 16.7 |
| 2. Strain 216 whole cells | 0.0 | 0.0 |

| Vaccine Group | % with foot-rot (lesions ≧2) | |
|---|---|---|
| | feet | sheep |
| 3. Strain 198 purified pili | 18.1 | 33.3 |
| 4. Strain 198 purified protease | 2.8 | 11.1 |
| 5. Strain 198 cell walls | 20.8 | 27.8 |
| 6. Strain 198 OMC | 4.2 | 11.1 |
| 7. Controls | 20.8 | 50.0 |

Against heterologous challenge with strain 216 (serogroup E) protection with purified protease was equivalent to that produced by the strain 198 (serogroup A) whole cell vaccine (group 1) and OMC vaccine (group 6). There were fewer feet and sheep with footrot (lesions >2) in the sheep vaccinated with strain 198 whole cells, purified protease, OMC, and strain 216 whole cells than in the controls.

Agglutinating antibody titres to strain 198 were elevated for sheep vaccinated with strain 198 whole cells, purified pili, and OMC. They were not elevated in sheep vaccinated with strain 198 protease, cell walls, or strain 216 whole cells. However agglutinating antibody titres to strain 216 were elevated in sheep (group 2) vaccinated with 216 whole cells.

| Vaccine Group | Mean agglutinin titres (28 days after vaccination and at challenge) | |
|---|---|---|
| | Strain 198 | Strain 216 |
| 1. Strain 198 whole cells | 5,920 | ≦400 |
| 2. Strain 216 whole cells | <200 | 26,605 |
| 3. Strain 198 purified pili | 8,063 | ≦400 |
| 4. Strain 198 proteases | <200 | <200 |
| 5. Strain 198 cell walls | <200 | ≦200 |
| 6. Strain 198 OMC | 11,403 | ≦400 |
| 7. Controls | <200 | NT |

NT—Not Tested

EXAMPLE 2

The experiment was conducted at the CSIRO Maribyrnong Field Station in an enclosed shed containing adjacent pens.

The Merino sheep were vaccinated twice subcutaneously in the neck region with an interval of 4 weeks between the injections.

Vaccines

The strain 198 cells used for preparing the vaccines were grown on TAS solid medium in Roux bottles.
1. Strain 198 whole cells $2 \times 10^9$ cells per dose.
2. Strain 198 whole cells acid precipitated, $2 \times 10^9$ cells per dose.
3. Strain 198 blended cells (virtually devoid of pili) $2 \times 10^9$ cells per dose.
4. Strain 198 supernatant containing pili and protease.
5. Strain 198 purified pili 30μ per dose.
6. Strain 198 outer membrane complex (OMC), 90μ per dose.
7. Strain 198 protease 25 and 50μ per dose.

The whole cells (group 1), supernatant (group 4) and purified protease (group 7) had substantial proteolytic activity whereas the other fractions did not. Since the antigenicity of the protease is relatively labile, all fractions were frozen at −70° C. and just prior to each vaccination they were mixed with aluminium hydroxide-oil adjuvant. The aqueous phase was mixed with an equal quantity of Alhydrogel and then emulsified with 2 parts of incomplete Freund's adjuvant (Difco).

The sheep were placed in large pens each of which contained one vaccinate from each group and 2 controls. Each vaccine group consisted of 10 sheep with 1 sheep from each of the vaccine groups being randomly allocated to each pen. All sheep were challenged 2 weeks after vaccination with strain 217 (serogroup C, subgroup 1) which has pilus agglutinogens serologically distinct from strains 198 and 216. Each foot of each sheep was challenged artificially with a culture of strain 217 grown on solid medium. Growth from half a plate was scraped onto a small piece of agar, placed on a pledget of cotton wool and bandaged between the claws of the hoof.

Results

Inspection of feet 46 days after challenge (60 days after second vaccination) showed the following results.

| Vaccine Group | % with severe foot-rot (lesions ≧3C) | |
|---|---|---|
| | feet | sheep |
| 1. Whole cells | 22.5 | 70 |
| 2. Acid precipitated cells | 22.5 | 30 |
| 3. Blended cells (depiliated) | 20.0 | 50 |
| 4. Supernatant (pili and protease) | 50.0 | 75 |
| 5. Purified pili | 40.0 | 70 |
| 6. OMC | 35.0 | 70 |
| 7. Purified protease | 15.0 | 40 |
| 8. Controls | 57.5 | 90 |

Against heterologous challenge with strain 217 (serogroup C, subgroup 1), protection with purified protease was equivalent to that produced by the whole cell vaccines and better than purified pili or OMC. In other words, there were fewer feet with severe foot-rot (lesions ≧3c) in the sheep vaccinated with either purified protease, whole cells, acid precipitated cells or blended cells than in the controls.

Agglutinating antibody titres were elevated for all vaccine groups except the protease vaccine group and the blended cell vaccine group.

| Vaccine Group | Mean agglutinin titres (14 days after vaccination and at challenge) Strain 198 |
|---|---|
| 1. Whole cells | 1,056 |
| 2. Acid precipitated cells | 8,445 |
| 3. Blended cells (depiliated) | ≦200 |
| 4. Supernatant (pili and protease) | 1,600 |
| 5. Purified pili | 18,102 |
| 6. OMC | 2,425 |
| 7. Purified protease | <200 |
| 8. Controls | <200 |

The purified protease vaccine induced specific antiprotease antibody in vaccinated sheep as determined by the Western immunoblot procedure (O'Donnell, et al 983) and agar gel immunodiffusion.

EXAMPLE 3

The experiment was conducted on irrigated pasture at the CSIRO Werribee Field Station.

Merino sheep were vaccinated three times subcutaneously in the neck region with 2 ml doses, with an interval of 3 and 4 weeks between injections.

Vaccines
1. Strain 198 whole cells, $2 \times 10^9$ cells per dose.
2. Strain 198 purified pili, 50μ per dose. 3. Strain 198 purified protease (isoenzyme band V2), 100, 50 and 50μ per dose.
4. Strain 198 purified proteases (mixture of isoenzyme bands V2, 3 and 5), 100, 50 and 50μ per dose.

The aqueous phase of the vaccines was mixed with an equal quantity of Alhydrogel and then emulsified with incomplete Freund's adjuvant (Difco) in the ratio 1:2.

There were 12 sheep per vaccine group and 12 sheep in the control group. The sheep were randomly allocated to each of the groups on a bodyweight basis. All groups were run as one flock, and were exposed 7 days after the second vaccination to donor sheep previously infected with B.nodosus strain 198, the same strain as used for preparing the above vaccines.

Results

Inspection of feet 48 and 103 days after challenge showed the following results:

| Vaccine Group | % with severe foot-rot (lesions ≧3C) | | | |
|---|---|---|---|---|
| | 48 days | | 103 days | |
| | feet | sheep | feet | sheep |
| 1. Strain 198 whole cells | 2.1 | 8.3 | 4.0 | 16.7 |
| 2. Strain 198 purified pili | 0.0 | 0.0 | 0.0 | 0.0 |
| 3. Strain 198 purified protease (band V2) | 20.8 | 33.3 | 12.5 | 25.0 |
| 4. Strain 198 purified proteases (bands V2, 3 and 5) | 6.3 | 16.7 | 0.0 | 0.0 |
| 5. Controls | 83.3 | 100.0 | 75.0 | 100.0 |

In all of the vaccine groups there were significantly fewer feet effected with lesions of severe footrot (≧3c) than in the control unvaccinated group at 48 or 103 days after challenge. However, at both inspections there were fewer feet affected with severe footrot in the group immunised with the mixture of protease isoenzymes (V2,3,5) than those immunised with isoenzyme V2. This was also reflected in the bodyweights of these 2 groups at the end of the experiment. The mean gain or loss in bodyweight for groups of sheep vaccinated with V2, the mixture of proteases, strain 198 purified pili and strain 198 whole cells was −1.87, +0.92, +2.4 and +1.47 kg respectively. The mean loss in bodyweight for the control vaccine group was 9.0 kg.

Agglutinating antibody titres were elevated for sheep vaccinated with whole cells and purified pili but not in those immunised with either of the 2 protease vaccines.

| Vaccine Group | Mean agglutinin titres against strain 198 antigen | |
|---|---|---|
| | 14 days after 2nd vaccination | 14 days after 3rd vaccination |
| 1. Strain 198 whole cells. | 1,902 | 5,079 |
| 2. Strain 198 purified pili. | 14,519 | 24,036 |
| 3. Strain 198 purified protease (band V2) | <200 | ≦400 |
| 4. Strain 198 purified (bands V2, 3 and 5) | <200 | <200 |
| 5. Controls | <200 | NT |

NT—Not Tested

The better performance of the protease V2,3,5 vaccine in comparison to V2 was reflected in the higher specific ELISA antibody titres against the mixture of proteases (6,166 and 658, respectively) 14 days after the third vaccination. Furthermore, in immunodiffusion analyses at least 1 precipitin line was evident when serums from sheep vaccinated with either V2 or V2,3,5 were reacted against purified V2 antigen whereas an extra non-cross reacting precipitin line was present when the serums from the V2,3,5 vaccine group but not in those from the V2 vaccine group were reacted against the mixture of proteases V2,3,5. Immunoblotting from non-dissociating polyacrylamide gels confirmed that V2 vaccine induced antibodies reactive against protease isoenzyme V2 whereas the mixture of protease isoenzymes (V2,3,5) induced antibodies reactive against isoenzymes V2 and V5. In immunodiffusion, immunoblotting and ELISA, V2 appeared to be antigenically similar to benign strain 305 (serogroup C, subgroup 2) isoenzyme B3 and B4 and different from V5 and B5 which were also antigenically similar.

| Sheep antiserums | ELISA antigen | | | | |
|---|---|---|---|---|---|
| | V2 | V5 | B3 | B4 | B5 |
| V2 | 620 | 550 | 1,700 | 2,350 | 385 |
| V5 | 830 | 9,200 | 2,300 | 3,125 | 10,000 |
| B3 | 1,900 | 1,150 | 2,700 | 4,800 | 1,000 |
| B4 | 2,150 | 1,900 | 3,300 | 6,000 | 1,600 |
| B5 | 40 | 6,800 | 870 | 830 | 6,500 |

CONCLUSION

Examples 1 and 2 above demonstrate that the proteases induce cross-protection against 2 serogroups (C and E) distinct from each other and the serogroup (A) from which the antigen was prepared. This suggests that the proteases have common antigens or serological determinants which are shared by at least some serogroups. Example 3 demonstrates that protection can be induced against a highly virulent strain of the homologous serogroup (A).

The proteases of B.nodosus are thus promising cross-protective antigens for providing broad-spectrum cover against a wide range of serogroups. The present invention extends to the use for vaccination against footrot of individual protease isoenzymes and mixtures of isoenzymes produced either by B.nodosus itself or through recombinant DNA technology which allows the transfer of the genes encoding the protease isoenzymes of B.nodosus into a new host. The new host in which the protease antigens are produced from cloned B.nodosus gene sequences may be another bacterium such as species selected from Bacillus, Escherichia and Pseudomonas or any other type of cell in which the genes are capable of being expressed (i.e. translated into the protein antigen product) with or without genetic modification of the host genes or additional genetic engineering of the cloned B.nodosus gene sequences themselves. Thus cloning of the proteases by recombinant DNA technology may provide the solution to the problem of producing large amounts of these antigens required for vaccine manufacture, and the present invention extends to the use of the proteases produced either by B.nodosus itself or by means of cloning of the antigens into a new host.

It is well known that it is often not necessary to use a whole protein antigen to generate antibodies active against that protein or the corresponding infectious agent. It is sometimes possible to use polypeptide fragments for this purpose. It is therefore within the ambit of this invention to use as the protease antigens related immunogenic fragments derived from modified *B.nodosus* genes, gene fragments expressed in the new hostor chemically synthesised peptides. The term "protease" as used throughout this specification and claims is therefore to be understood as extending to include such immunogenic fragments.

It will be appreciated by those skilled in the art that the proteases produced by *B.nodosus* offer several advantages over other antigens for inducing protection, particularly the pili antigens. In particular:

(a) the proteases are relatively small proteins,
(b) the proteases from at least some of the different serogroups have common antigenic determinants, and
(c) the proteases are excreted by *B.nodosus* outside the cell into the culture medium.

REFERENCES

Broad, T. E. and Skerman, T. M. Partial purification and properties of extracellular proteolytic activity of *Bacteroides nodosus*. *N. Z. Journal of Agricultural Research*, (1976), 19:317–322.

Claxton, P. D., Ribeiro, L. A. and Egerton, J. R. Classification of *Bacteroides nodosus* by agglutination tests. *Australian Veterinary Journal*, (1983), 60:331–334.

Davis, B. J. Disc electrophoresis. II. Method and application to human serum proteins. *Annals of the New York Academy of Sciences* (1964) 121:404–427.

Depiazzi, L. J. and Richards, R. B. A degrading protease test to distinguish benign and virulent ovine isolates of *Bacteroides nodosus*. *Australian Veterinary Journal*, (1979), 55:25–28.

Depiazzi, L. J. and Rood, J. I. The thermostability of proteases from virulent and benign strains of *Bacteroides nodosus*. *Veterinary Microbiology*, (1984), 9:227–236.

Every, D. Proteinase isoenzyme patterns of *Bacteroides nodosus*: Distinction between ovine virulent isolates, ovine benign isolates and bovine isolates. *Journal of General Microbiology*, (1982), 128:809–812.

Every, D. and Skerman, T. M. Protection of sheep against experimental footrot by vaccination with pili purified from *Bacteroides nodosus*. *New Zealand Veterinary Journal*, (1982), 30:156–158.

Fahey, K. J., McWaters, P. G., Stewart, D. J., Peterson, J. E. and Clark, B. L. Quantitation by ELISA of pili and sheep antibodies to the pili of *Bacteroides nodosus*. *Australian Veterinary Journal*, 1983, 60:111–116.

Hartree, E. F. Determination of Protein: A modification of the Lowry Method that gives a linear photometric response. *Analytical Biochemistry*, (1972), 48:422–427.

Kortt, A. A., Burns, J. E. and Stewart, D. J. Detection of the extracellular proteases of *Bacteroides nodosus* in polyacrylamide gels: a rapid method of distinguishing virulent and benign ovine isolates. *Research in Veterinary Science*, (1983), 35:171–174.

Kortt, A. A., O'Donnell, I. J., Stewart, D. J. and Clark, B. L. Activities and partial purification of extracellular proteases of *Bacteroides nodosus* from virulent and benign footrot. *Australian Journal of Biological Sciences*, (1982), 35:481–489.

O'Donnell, I. J., Stewart, D. J. and Clark, B. L. Serological identification of pilus antigen and other protein antigens of *Bacteroides nodosus* using electro-blot radioimmunoassay after electrophoretic fractionation of the proteins on sodium dodecyl sulfate polyacrylamide gels. *Australian Journal of Biological Sciences*, (1983), 36:15–20.

Stewart, D. J. The role of various antigenic fractions of *Bacteroides nodosus* in eliciting protection against footrot in vaccinated sheep. *Research in Veterinary Science*, (1978), 24:14–19.

Stewart, D. J., Clark, B. L., Emery, D. L., Peterson, J. E. and Fahey, K. J. A *Bacteroides nodosus* immunogen, distinct from the pilus, which induces cross-protective immunity in sheep vaccinated against footrot. *Australian Veterinary Journal*, (1983a), 60:83–85.

Stewart, D. J., Clark, B. L. and Jarrett, R. G. Observations on strains of *Bacteroides nodosus* of intermediate virulence to sheep. *Australian Advances in Veterinary Science*, (1982), pp. 219–222.

Stewart, D. J., Clark, B. L., Peterson, J. E., Emery, D. L., Smith, E. F., Griffiths, D. A. and O'Donnell, I. J. The protection given by pilus and whole cell vaccines of *Bacteroides nodosus* strain 198 against ovine footrot induced by strains of different serogroups. *Australian Veterinary Journal*, (1985), (Accepted for publication).

Stewart, D. J., Clark, B. L., Peterson, J. E., Griffiths, D. A. and Smith, E. F. Importance of pilus-associated antigen in *Bacteroides nodosus* vaccines. *Research in Veterinary Science*, (1982), 32:140–147.

Stewart, D. J., Clark, B. L., Peterson, J. E., Griffiths, D. A., Smith, E. F. and O'Donnell, I. J. Effect of pilus dose and type of Freund's adjuvant on the antibody and protective responses of vaccinated sheep to *Bacteroides nodosus*. *Research in Veterinary Science*, (1983b), 35:130–137.

Thorley, C. M. and Egerton, J. R. Comparison of alum-absorbed or non-alum-absorbed oil emulsion vaccines containing either pilate or non-pilate *Bacteroides nodosus* cells in inducing and maintaining resistance of sheep to experimental foot-rot. *Research in Veterinary Science*, (1981), 30:32–37.

We claim:

1. A vaccine for use in the protection against or treatment of foot-rot, comprising an immunologically effective amount of at least one protease of *Bacteroides nodosus* as an active component thereof and an acceptable pharmaceutical or veterinary carrier thereof.

2. A vaccine according to claim 1, wherein said protease is an extracellular serine protease of *Bacteroides nodosus*.

3. A vaccine according to claim 1, comprising a mixture of two or more of said proteases.

4. A vaccine according to claim 3, wherein said proteases are derived from one or more virulent, intermediate, or benign strains of *Bacteroides nodosus*.

5. A vaccine according to any one of claims 1 to 4, further comprising an adjuvant.

6. A vaccine according to claim 5, wherein said adjuvant is an oil, saponin-aluminium hydroxide, or aluminium hydroxide-oil adjuvant.

7. A vaccine according to claim 1, wherein said protease is derived from virulent Strain 198 of *Bacteroides nodosus*.

8. A vaccine according to claim 7, comprising Strain 198 purified protease isoenzyme band V2.

9. A vaccine according to claim 7, comprising a mixture of Strain 198 purified protease isoenzyme Bands V2, V3 and V5.

10. A vaccine according to claim 1, wherein said protease is prepared by purification from the supernatant of an anaerobically grown, CaCl$_2$-containing broth culture of *Bacteroides nodosus*.

11. A vaccine according to claim 10, wherein the culture medium used is a TAS (trypticase-arginine-serine) broth culture containing CaCl$_2$.

12. A vaccine for use in protection against or treatment of foot-rot, comprising an immunologically effective amount of at least one purified protease isoenzyme of *Bacteroides nodosus* as an active component thereof and an acceptable pharmaceutical or veterinary carrier thereof.

13. A vaccine according to claim 12, wherein said protease is an extracellular serine protease of *Bacteroides nodosus*.

14. A vaccine according to claim 12, comprising a mixture of two or more of said proteases.

15. A vaccine according to claim 14, wherein said proteases are derived from one or more virulent, intermediate, or benign strains of *Bacteroides nodosus*.

16. A vaccine according to any one of claims 12 or 13, further comprising an adjuvant.

17. A vaccine according to claim 16, wherein said adjuvant is an oil, saponin-aluminum hydroxide, or aluminum hydroxide-oil adjuvant.

18. A vaccine according to claim 12, wherein said protease is derived from virulent Strain 198 of *Bacteroides nodosus*.

19. A vaccine according to claim 18, comprising Strain 198 purified protease isoenzyme band V2.

20. A vaccine according to claim 18, comprising a mixture of Strain 198 purified protease isoenzyme Bands V2, V3 and V5.

21. A vaccine according to claim 12, wherein said protease is prepared by purification from the supernatant of an anaerobically grown, CaCl$_2$-containing broth culture of *Bacteroides nodosus*.

22. A vaccine according to claim 21, wherein the culture medium used is a TAS (trypticase-arginine-serine) broth culture containing CaCl$_2$.

23. A method of protection against or treatment of foot-rot, which comprises the administration of a vaccine according to any one of claims 1 to 4, 7 to 11, and 15.

24. A method of protection against or treatment of foot-rot which comprises administering of an immunologically effective amount of at least one protease of *Bacteroides nodosus* and an acceptable pharmaceutical or veterinary carrier therefor.

25. A method of protection against or treatment of foot-rot, which comprises administering of a vaccine according to any one of claims 12, 13–15 or 18–22.

26. A method of protection against or treatment of foot-rot, which comprises administering of a vaccine according to claim 5.

27. A method of protection against or treatment of foot-rot, which comprises administering of a vaccine according to claim 16.

* * * * *